(12) United States Patent
Nier et al.

(10) Patent No.: US 6,911,007 B2
(45) Date of Patent: Jun. 28, 2005

(54) METHOD FOR DETERMINING CONCENTRATION; A DIALYSER

(75) Inventors: Volker Nier, Rosbach (DE); Matthias Kraemer, Friedrichsdorf (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 377 days.

(21) Appl. No.: 10/025,983

(22) Filed: Dec. 26, 2001

(65) Prior Publication Data

US 2003/0045827 A1 Mar. 6, 2003

(30) Foreign Application Priority Data

Dec. 22, 2000 (DE) .......................... 100 64 179
Mar. 23, 2001 (DE) .......................... 101 14 283

(51) Int. Cl.$^7$ .................... A61B 5/00; A61M 37/00
(52) U.S. Cl. ................... 600/309; 600/366; 604/4.01
(58) Field of Search .................. 600/309, 348, 600/366; 604/29, 4.01, 507; 210/321.6

(56) References Cited

U.S. PATENT DOCUMENTS

| | | | | |
|---|---|---|---|---|
| 3,912,455 A | * | 10/1975 | Lichtenstein ................ 600/578 |
| 3,934,977 A | * | 1/1976 | Cleaver ........................ 436/74 |
| 3,953,172 A | * | 4/1976 | Shapiro et al. ............. 436/500 |
| 4,309,417 A | | 1/1982 | Staples ........................ 424/128 |
| 4,618,587 A | * | 10/1986 | Premoli et al. .......... 205/781.5 |
| 4,724,216 A | * | 2/1988 | Young et al. ............... 210/698 |
| 5,714,060 A | | 2/1998 | Kenley et al. .............. 210/194 |
| 5,780,438 A | * | 7/1998 | Gilchrist et al. ............. 514/21 |
| 6,274,382 B1 | | 8/2001 | Treiber ......................... 436/74 |
| 6,325,774 B1 | | 12/2001 | Bene et al. ................ 604/4.01 |

FOREIGN PATENT DOCUMENTS

| | | |
|---|---|---|
| DE | 689 16 561 | 10/1994 |
| EP | 0 330 892 | 9/1989 |
| EP | 0 898 976 | 3/1999 |
| EP | 0 952 453 | 10/1999 |
| WO | 91/06326 | 5/1991 |

OTHER PUBLICATIONS

Togawa, Tatsuo. "Patient Monitoring" Wiley Encyclopedia of Electrical and Electronics Engineering Online. Dec. 27, 1999.*
Morita et al.; Regional Anticoagulation During Hemodialysis Using Citrate; The American Journal of the Medical Sciences; 1961; pp. 72–83.
Heparin Anticoagulation in Chronic Hemodialysis Patients; Kidney international, vol. 49 (1996), pp. 806–813.
Mehta et al.; Regional Citrate Anticoagulation for Continuous Arteriovenous Hemodialysis in Critically Ill Patients; Kidney International, vol. 38 (1990), pp. 976–981.

* cited by examiner

Primary Examiner—Eric F. Winakur
Assistant Examiner—Matthew Kremer
(74) Attorney, Agent, or Firm—Jacobson Holman PLLC

(57) ABSTRACT

A method for determining the concentration of an ion, atom or molecule bound in a complex. A reliable determination of the concentration of the ion, atom or molecule to be determined is possible in accordance with the invention in that the complexing of the ion, atom or molecule is prevented at least during the determination of the concentration by the addition or withdrawal of a substance. Also contemplated is a dialyser having a haemo-dialyser and/or a haemo-filter and an extra-corporal blood circulation with which a device for the adding of citrate to the blood is connected upstream and a device for the adding of a substitution solution containing ions to the blood is connected downstream of the haemo-dialyser and/or of the haemo-filter. Ion concentration in the dialysate downstream of the haemo-dialyser and/or of the haemo-filter is detected with respect to the direction of flow of the dialysate.

17 Claims, 3 Drawing Sheets

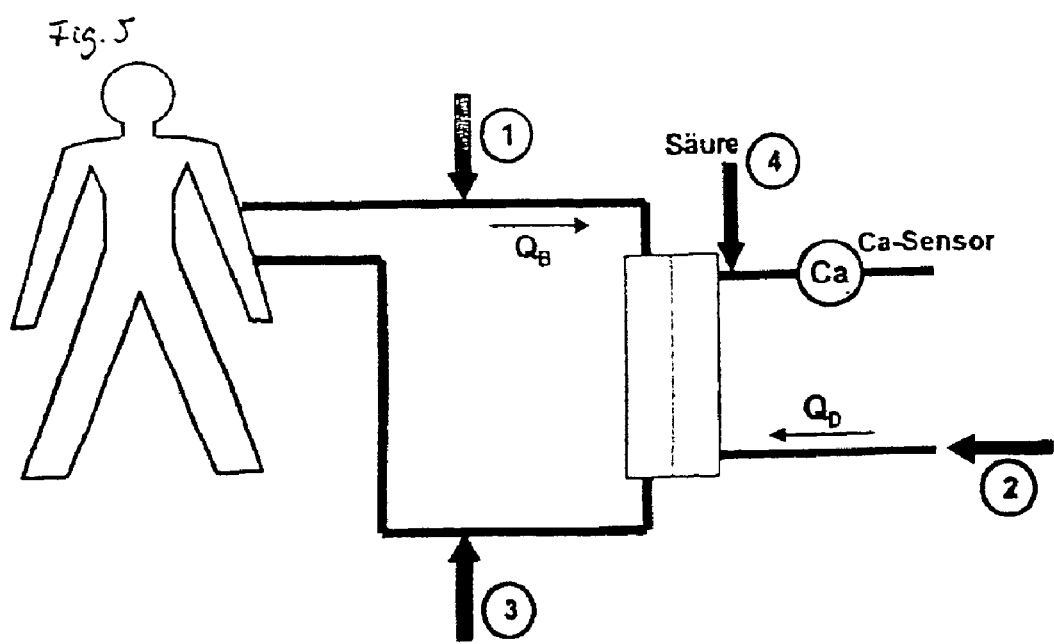

METHOD FOR DETERMINING CONCENTRATION; A DIALYSER

BACKGROUND OF THE INVENTION

1. Field of the Invention

The present invention relates to a method for determining the concentration of an ion, atom or molecule bound in a complex.

2. Description of the Related Art

Numerous ions, atoms and molecules are not present in isolated form, but in the form of the most different complexes. This relates to ions, atoms and molecules both in the blood circulation of a patient and in the blood that is taken from the patient for the purpose of a certain blood treatment or patient treatment and has suitable complex agents added outside the body.

An example for the complexing of ions is so-called citrate anti-coagulated haemodialysis/haemofiltration. Here, a complexing of $Ca^{++}$ ions of the blood takes place in the extra-corporal blood circulation by means of citrate in order to inhibit blood clotting during the treatment, above all during the blood/membrane contact in the dialyser.

Inhibition of blood clotting is required with most haemo-dialysis patients today. The standard is to use non-fractioned heparin that is infused into the arterial side of the extra-corporal hose system by a syringe pump. The use of both non-fractioned heparin and alternative anti-coagulants such as low-molecular-weight heparin or hirudin is problematic for some of the patients and for other extra-corporal blood therapies for the following reasons:

Anti-coagulation has a systemic effect (that is not only on membrane contact in the extra-corporal circulation, but in the whole body), which results in critical haemorrhage risk for some patients. In particular in the intensive medical area, 30 to 40% of patients are at risk of haemorrhage.

Some patients show incompatibility reactions such as heparin-induced thrombocytopenia which exclude the use of these anti-coagulants.

Adsorptive therapies (for example liver replacement therapy) can be incompatible with the use, for example, of heparin if this neutralises the binding points of the adsorber (provided for the adsorption of toxins).

An alternative which avoids the problems listed is regional clotting inhibition (only in the extra-corporal circulation, above all during the blood/membrane contact) by citrate. In this method shown in FIG. 1, the concentration of free calcium (Ca) is reduced by so much by the addition of tri-sodium citrate at the point in accordance with Pos. 1 in FIG. 1 that the clotting cascade is interrupted, with two citrate molecules in case forming a complex with three Ca ions. The use of Ca-free dialysate in accordance with Pos. 2 in FIG. 1 and the Ca withdrawal this causes also contributes to the concentration reduction. To avoid depletion of the body with respect to Ca and Mg (which is also bound by citrate), a further solution (see Pos. 3 in FIG. 1) containing Ca ions and Mg ions in an adapted concentration must be infused into the venous side of the extra-corporal circulation or into a separate venous entry.

Clinical studies [Morita Y, Johnson R W, Doren R E, Hall D S, "Regional anticoagulation during hemodialysis using citrate". The American Journal of the Medical Sciences (1961); Janssen M J M F et al., "Citrate compared to low molecular weight heparin anticoagulation in chronic hemodialysis patients", Kidney Int (1996) 49:806–813; Mehta R L, McDonald B R, Aguilar M M, Ward D M, "Regional citrate anticoagulation for continuous arteriovenous hemodialysis in critically ill patients", Kidney Int (1990) 38:976–981] demonstrate that regional citrate anti-coagulation very effectively prevents blood clotting in the extra-corporal circulation. At the same time, an increased risk of haemorrhage for the patient is avoided. Citrate dialysis is therefore seen as an interesting, effective alternative to conventional heparin anti-coagulation for that part of the patient population in which—as described above—the use of heparin is disadvantageous or clearly contra-indicated.

Despite these clear therapeutic advantages, citrate anti-coagulation has only been used to a low extent up to now and not as an automated, standardised process. The reasons for this are:

1. The increased effort: in conventional dialysis, standard haemo-dialysis solution and a low amount of heparin is required. In citrate dialysis, three solutions are usually required: the haemo-dialysis solution free of Ca and Mg and adapted in the Na and bicarbonate content, the tri-sodium citrate solution and the $Ca^{++}/Mg^{++}$ solution.
2. Safety aspects in the dosing of the $Ca^{++}/Mg^{++}$ solution: if an incorrect dose is given here, a life-threatening situation can quickly arise (tetany, cardiac irregularity, cardiac arrest). Incorrect dosing can arise as a result of technical problems (e.g. failure of the pump, leaks, etc.), or by an incorrect determination of the Ca requirement.
3. Consequences of a supply of citrate or of the $Ca_3$—$Ci_2$ or $Mg_3$—$Ci_2$ complexes: metabolic alkalosis, non-physiological Ca concentration.

The increased effort of the process can be limited by a suitable technical realisation; certain additional costs are quite justified in patients with heparin incompatibilities. The supply of citrate or of citrate complexes can be greatly reduced by efficient withdrawal via the membrane (use of a large-area high-flux filter, possibly in combination with post-dilution HDF). A low remaining supply can probably be tolerated; if not, it can also be estimated and compensated by suitable modelling of the dialysis process and of the metabolisation of the complexes.

A citrate anti-coagulated dialysis method is known from WO 91/06326. Tri-sodium citrate is added to the arterial supply line of the extra-corporal blood circulation as the anti-coagulant, with the added amount of tri-sodium citrate per time unit only being adapted to the blood stream rate in the extra-corporal circulation. If the blood stream rate increases or falls, the addition rate of tri-sodium citrate is also increased or lowered respectively. The calcium ion concentration of the patient blood is not monitored in a close-meshed manner here, but determined in fairly large time intervals by blood samples. Since a close-meshed or continuous monitoring of the calcium concentration in the blood of the patient is missing and since the amount of added citrate is oriented only on the blood flow rate and not on the calcium level of the patient, it cannot be reliably precluded in this previously known method that calcium values result in the patient's blood which are non-physiological and which can accordingly bring about life-threatening consequences for the patient.

While ion-sensitive sensors are known by means of which the calcium ion concentration or the magnesium ion concentration in the blood of a patient can also be determined in small time intervals, the use of a sensor on the blood side is, however, disadvantageous and therefore undesirable due to a possible toxicity, as a result of sterility demands and for cost reasons.

It can also be necessary to make a concentration determination of ions, atoms or molecules bound in complexes in other applications than dialysis. Even under the assumption that ion-sensitive sensors could be used without disadvantages for the patient, their use in the determination of the concentration of complexed ions frequently does not deliver any results, or any results which can be utilised, since the properties of the ion present in the complex do not allow a meaningful measurement.

SUMMARY OF THE INVENTION

It is therefore the object of the present invention to provide a method for determining the concentration of an ion, atom or molecule bound in a complex by means of which the concentration of the ion, atom or molecule to be determined can be reliably found.

This object is solved by a method for determining the concentration of an ion, atom or molecule bound in a complex in which the complexing of the ion, atom or molecule is prevented at least during the concentration determination by adding or withdrawing a substance. The present invention thus has the underlying idea for the purpose of determining the concentration of avoiding the formation of the complex with the ion, atom or molecule or of separating the ion, atom or molecule from such a complex in order then to make the corresponding concentration determination.

The added substance can be an acid. The complexing is in this case prevented by the change in pH associated with the addition of the acid, with the complexing agent being protonated and thus, as it were, deactivated for the complexing of the substance to be determined.

The complexing can be prevented in that the addition of the complexing agent is interrupted or the complexing agent enters into a complex with another substance to be added and in this respect releases the ion, atom or molecule whose concentration is to be determined. The addition of a substance would thus be thinkable which has a higher affinity to the complexing agent than the ion, atom or molecule to be determined. The latter are "separated" from the complex on the addition of this substance and are then available for a measurement.

In another aspect of the present invention, provision is made that it is a method for determining the ion concentration of the blood of a patient in citrate anti-coagulated haemo-dialysis and/or haemo-filtration. In accordance with the invention, the ion concentration of the blood is here determined on the basis of the determination of the ion concentration in the dialysate. Before the ion concentration in the dialysate is determined, the complexing of the relevant ion is prevented by citrate for the purpose of determining the concentration.

In this way, the ion concentration of the blood of a patient can be monitored at a favourable cost and without safety risks for the patient during the treatment.

Due to the fact that the determination of the ion concentration does not take place in the blood of the patient, but in the dialysate, the substantial advantage results that sensors for measuring the blood/ion concentration and the above-mentioned disadvantages resulting therefrom can accordingly be avoided. It is therefore not necessary to interfere with the extra-corporal blood circulation in order to determine the concentration. This applies correspondingly to the repeated taking of blood samples not required here.

In accordance with a preferred aspect of the present invention, the complexing is prevented in that the citrate addition into the blood circulation is temporarily interrupted. Since the concentration in the dialyser on the blood side does not correspond to the concentration in the patient and since the ions, in particular the Ca ions and Mg ions, are bound to citrate by the complexing, the citrate infusion is interrupted in accordance with this embodiment in order to also obtain the actual ion concentration of Ca or Mg in the dialyser. The interruption of the citrate addition or of the citrate infusion can take place in regular intervals. The infusion of the Ca ions and Mg ions can be maintained in these intervals since the ions released by the interruption of the citrate addition are largely withdrawn from the blood in the dialyser. The infusion of the Ca ions and of the Mg ions can also be reduced in order to just compensate the partial withdrawal in the dialyser. This monitoring method is discontinuous since the citrate infusion can only be interrupted for short intervals in order to ensure sufficient anti-coagulation. However, this is sufficient to recognise critical trends in time. In the event of under-dosing or over-dosing, or total failure of the Ca/Mg ion infusion, it namely takes some time until critical concentrations are reached in the body. This time lies at around ten minutes and depends above all on the blood flow.

In a further aspect of the present invention, provision is made that the complexing is prevented in that the ion is released from the ion/citrate complex in the dialysate by lowering the pH. The concentration of the ion released in this way is subsequently determined. Such an embodiment of the present invention has the advantage that an interruption of the citrate infusion is not necessary here. If the relevant ion, preferably $Ca^{++}$ and/or $Mg^{++}$, is released from the ion/citrate complex, the corresponding ion can be determined without problem in the dialysate. The method is, however, relatively complex since an additional infusion is necessary in order to effect the release. Acid must be added on the dialysate side here. In addition, the ion/citrate complex is relatively large with a molecular weight of 504 (with Ca ions) so that a clearance is much lower than for electrolytes. The measurement or estimate of the blood side concentration from the dialysate concentration is then correspondingly more difficult. When setting a suitable pH, care is to be taken that the Ca ion or Mg ion is released as fully as possible since an only part release would result to blood concentration values which would be too low.

In another aspect of the present invention, provision is made that after the interruption of the citrate addition, the measurement of the ion concentration in the dialysate is carried out at the end of a length of time which is composed of a dead time determined by dead volumes and of a period of time required to achieve a quasi-stationary state. The dead volume results from the volumes of the hose connection between the infusion site for citrate and the cite of the measuring point for the corresponding ion concentration. Normally, dead times are to be expected in the range from around 10 to 30 s. The concentration on the dialysate side increases thereafter. This increase is not abrupt, but time constants of around 1 to 2 min. are to be anticipated until a quasi-stationary state is achieved. A state is to be understood by this from which changes in the concentrations are negligibly small or lie within a pre-determined tolerance.

In accordance with a preferred aspect of the present invention, provision is made that after the interruption of the citrate addition, the measurement of the ion concentration in the dialysate is repeated a multiple of times and the measured value is determined on the reaching of a quasi-stationary state. The concentration in the dialysate is thus measured at a plurality of times, a concentration course is determined in this way and it can then be evaluated whether the equilibrium concentration is achieved with sufficient precision.

In another aspect of the present invention, provision is made that after the interruption of the citrate addition, the measurement of the ion concentration in the dialysate is repeated a multiple of times and the measured value is determined by extrapolation of the ion concentration obtained in the dialysate. With this method, the equilibrium value is thus extrapolated from an increase behaviour of the concentration in the dialysate measured over a sufficient interval of time. This procedure has the advantage that it is not necessary to wait for the equilibrium to be adopted. However, a knowledge of the time behaviour of the concentration increase is required here.

In accordance with another preferred aspect, the citrate concentration can be interrupted for a pre-determined time interval and the measured value is determined by integration of the area of the response function defined by the ion concentration in the dialysate as a function of time. The citrate infusion can be interrupted, for example, for a fixed, relatively short time interval, approximately 1 to 2 min. A conclusion can then be made as to the equilibrium concentration by evaluation of the area under a pulse-like response function of the concentration in the dialysate.

The measure of the intermittent interruption of the citrate infusion naturally also interrupts the regional anti-coagulation in the dialyser. However, it cannot be anticipated that the a substantial impairment of the anti-coagulation would result from this. For instance, in the so-called dialysis free of heparin, for example, which is actually a completely anti-coagulation-free dialysis with a cyclic rinsing of the extra-corporal circulation, the complication rate due to blood clotting is relatively low (less than 5%). It is therefore not to be anticipated that an intermitting interruption of anti-coagulation, which could then amount in sum to a total of approximately 10 to 20% of the dialysis time, would result in clinical problems.

If complexing is prevented or opened in that the ion is released from the ion-citrate complex in the dialysate by lowering the pH, a pH of 2 to 3 is preferably set since here a correspondingly complete dissociation of the complex can be realised.

The setting of a pH in the dialysate preferably takes place by means of an infusion of acid.

It is particularly advantageous if the dialysate flow is reduced for the purpose of approximating the ion concentration of the dialysate to the ion concentration of the blood of the dialysate flow. The ion concentration on the dialysate side is adapted to the ion concentration on the blood side by a reduction of the dialysate flow.

It was shown theoretically and experimentally that when there is a reduction in the dialysate flow with an unchanging blood flow, the concentration of low-molecular-weight substances approaches the blood plasma concentration more and more. If the dialysate flow is selected to be sufficiently low—dependent on the blood flow, the molecule in question and the dialyser used—the dialysate concentration is practically identical to the blood concentration; the dialysate then reaches saturation. In the case of ions, the dialysate concentration will, however, differ by some percent from the blood/plasma concentration in this state of the flow equilibrium due to the Donnan effect, which can be taken into account mathematically with knowledge or estimation of the plasma protein content.

In another aspect of the present invention, provision is made that the determination of the ion concentration of the blood takes place without a reduction in the dialysate flow by calculation. Such a procedure has the advantage that the dialysate flow does not need to be lowered and thus the dialysis efficiency is not reduced in this time interval.

Under normal treatment conditions, in which the dialysate flow is larger than or equal to the blood flow, a lower dialysate concentration results with respect to the blood concentration. With knowledge of the dialyser transport properties for the observed molecule/atom ($k_0A$), of the machine settings (blood and dialysate flow) and of the haematocrit, the blood plasma concentration can be calculated in a good approximation from the measured concentration on the dialysate side. With knowledge of the clearance, the concentration on the blood side is calculated from the simple formula $$C_{Bi} := (Q_D/K) * C_{Do}$$

where $C_{Bi}$ is the entry concentration on the blood side, $C_{Do}$ is the measured exit concentration on the dialysate side, $Q_D$ is the dialysate flow and K is the clearance. K is given for an in vitro situation with a purely diffusing transfer by:

$$K := Q_B \cdot \frac{\exp\left[k0A \cdot \left(\frac{1}{Q_B} - \frac{1}{Q_D}\right)\right] - 1}{\exp\left[k0A \cdot \left(\frac{1}{Q_B} - \frac{1}{Q_D}\right)\right] - \frac{Q_B}{Q_D}}$$

Corresponding, more complex formulae are also available for the in vivo situation, likewise for haemodialysis with ultra-filtration and for filtration (HF) or combined filtration/diffusion (HDF) processes. This mathematical formula, which can be used for any desired dialysis situation, has been validated with in vitro and in vivo measurements and is available in a user-friendly form in the form of the software "Clearance Calculation Tool CCT" from FMC.

The possibility of reducing the dialysate flow is to be preferred when a precise measurement is required. However, it has the disadvantage that the dialysate flow has to be lowered for some minutes and that thus the dialysis efficiency is reduced correspondingly in this time interval. If, however, no very precise measurements are required for a monitoring of the Ca ion concentration, the method of calculating the ion concentrations without lowering the dialysate flow can also be used in which, accordingly, no influencing of the dialysis by the measuring method takes place, except for the intermittent interruption of anti-coagulation.

It is particularly advantageous if the detection of the ion concentration in the dialysate takes place by means of an ion-sensitive sensor in the dialysate flowing from the dialyser. The precision of the determination of the ion concentration of the blood is essentially given by the sensor system. Since an incorrect display of the sensor in combination, for example, with an incorrect dosing represents a high potential risk for the patient, the function of the sensor must be ensured by a suitable test or by other measures. A repeated function test of the sensor during dialysis can be necessary, with the test intervals being able to be oriented on the time interval within which a critical state can develop for the patient (some 10 minutes). Alternatively, or additionally, redundant sensor systems can be used. It is also possible to provide security systems which immediately detect and put on display a characteristic failure behaviour of the sensor.

In another aspect of the present invention, provision is made that the determined ion concentration of the blood of a patient serves as a controlled variable whose value is influenced by the control variables of citrate addition and/or addition of a substitution medium containing ions. A closed loop can thus be realised with a corresponding regulating unit here by which a desired value of the concentration of Ca ions and/or Mg ions can be set in the patient's blood. An independently operating monitoring system for the haemo-dialysis and/or haemo-filtration anti-coagulated by citrate can be realised in this way by which a physiological value of the concentration of Ca ions and/or Mg ions can always be set in the patient's blood. The citrate addition or the addition of the corresponding substitution medium containing ions can serve as the control variables. However, when selecting the citrate addition as the control variable, it must be considered that these must not fall below certain limits in order to keep the ion concentrations low in the region of the dialyser, which is necessary in order to effectively avoid coagulation.

A particularly reliable embodiment of the following invention results from an alarm being triggered when the ion concentration determined in the blood of the patient lies outside a permitted range or differs from a permitted value. An alarm can be triggered when an individual measurement results in critically high or low values or when a critical trend is determined. Additionally or alternatively to an alarm, suitable counter-measures can be initiated such as a bypassing of the machine, stopping of the infusions, changing of the infusion rates, etc.

In another aspect of the invention, provision is made that the ion concentration in the compartment of the dialyser on the blood side is determined without an interruption to the citrate supply and is compared with a permitted threshold value and the citrate supply is changed in dependence on this comparison. Such a procedure is meaningful to check whether the citrate addition is sufficient to lower the Ca ion concentration by so much that the coagulation risk is reduced to the desired level. This naturally has to be determined with the citrate supply switched on since the excess free Ca has to be determined with citrate supply. A regulating system is possible here which automatically varies the citrate infusion rate in accordance with the measured Ca ion concentration. The required Ca/Mg ion substitution can also be determined in this way.

As stated above, the ions are preferably calcium ions and/or magnesium irons which are both bound in corresponding complexes by citrate. The method is preferably carried out while determining the Ca ion concentration in the dialysate.

The present invention further relates to a dialyser having a haemo-dialyser and/or a haemo-filter and having an extra-corporal blood circulation, with which means for the adding of citrate to the blood are connected upstream of the haemo-dialyser and/or of the haemo-filter and means for the adding of a substitution solution containing ions to the blood are connected downstream of the haemo-dialyser and/or of the haemo-filter, and having a dialysate line which has means to detect an ion concentration in the dialysate downstream of the haemo-dialyser and/or of the haemo-filter with respect to the direction of flow. The means for detecting the ion concentration are preferably designed as one or more ion-sensitive sensors. A redundant design increases the operational reliability of the dialyser and allows the fast recognition of incorrect measurements.

A reliable embodiment of the dialyser can be realised in that a test device is provided which makes a functional check of the sensor(s) in time intervals or on actuation by an operator.

Means can be in communication with the dialysis line for the addition of a substance by which the pH of the dialysate can be changed. In this way, the ion to be determined can be determined by the pH change in its concentration after its release from the complex.

The means for the addition of the substance can be disposed such that the addition takes place downstream of the dialyser with respect to the direction of flow of the dialysate.

In accordance with another aspect of the present invention, means are provided by which the dialysate flow can be temporarily reduced. The ion concentration in the blood can be calculated particularly precisely from the ion concentration in the dialysate by the reduction in the dialysate flow.

A control unit can be provided which controls the means for the addition of citrate to the blood in time intervals or on actuation by the operator such that the addition is temporarily interrupted and which after the start of the interruption of the citrate addition records the concentration value determined by the means for detecting an ion concentration in the dialysate continuously or in time intervals.

The control unit can be designed such that this determines the measured value of the $Ca^{++}$ ion concentration in accordance with a method in accordance with claims 7 to 10.

In accordance with another preferred design of the present invention, a regulating unit can be provided which is connected to the ion-sensitive sensor and to the means for adding citrate and/or to the means for adding a substitution solution containing ions and which initiates an increase or decrease in the addition amount of citrate and/or of substitution solution containing ions in dependence on the comparison between a nominal value or a nominal value range and the determined actual value of the ion concentration. In this way, the concentration in the blood of the patient can be regulated to a desired value or in a desired interval.

The regulating unit and/or the means for the addition of citrate can be designed such that the concentration of citrate cannot be lowered below a threshold value. It is prevented in this way that the citrate concentration does not fall below a certain value which is required for the effective prevention of coagulation.

An alarm device can be provided which triggers an alarm on determination of a critical individual measurement of the ion concentration or on determination of a critical trend of individual measurements. The operator's attention is thus drawn to such a critical state, for example acoustically and/or visually.

BRIEF DESCRIPTION OF THE DRAWINGS

Further details and advantages of the present invention are explained in more detail by means of an embodiment illustrated in the drawing, There are shown:

FIG. 5 a schematic representation of a haemo-dialysis method having anti-coagulation by citrate; determination of the Ca ion concentration by dissociation of the Ca citrate complexes in the dialysate.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
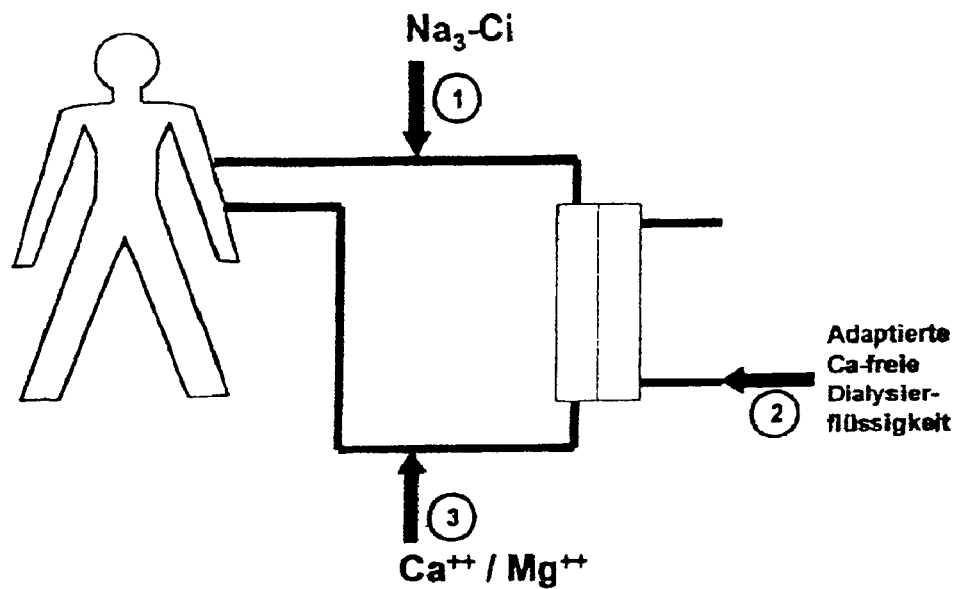
FIG. 1: a schematic representation of a haemo-dialysis method having citrate anti-coagulation with solutions used and the position of the supply.

FIG. 1 shows a haemo-dialysis method with anti-coagulation by citrate in a schematic representation. By the addition of tri-sodium citrate (see Pos. 1) in the part of the extra-corporal circulation which leads from the patient to the dialyser, the concentration of free Ca ions is reduced by so much that the clotting cascade is interrupted. A tri-calcium bicitrate complex is created. A further reduction in the concentration of Ca ions in the blood is caused in that dialysate free of Ca (see Pos. 2) is used so that a correspondingly high gradient of the Ca ion concentration over the membrane results. In order to avoid a non-permitted depletion of calcium, and also magnesium which is also bound by citrate, in the body of the patient, a substitution solution (see Pos. 3), which contains the Ca ions and Mg ions in an adapted concentration, is infused into the venous side of the extra-corporal circulation. The corresponding substitution solution can naturally also be infused into a separate venous entry of the patient.

Figure 2:
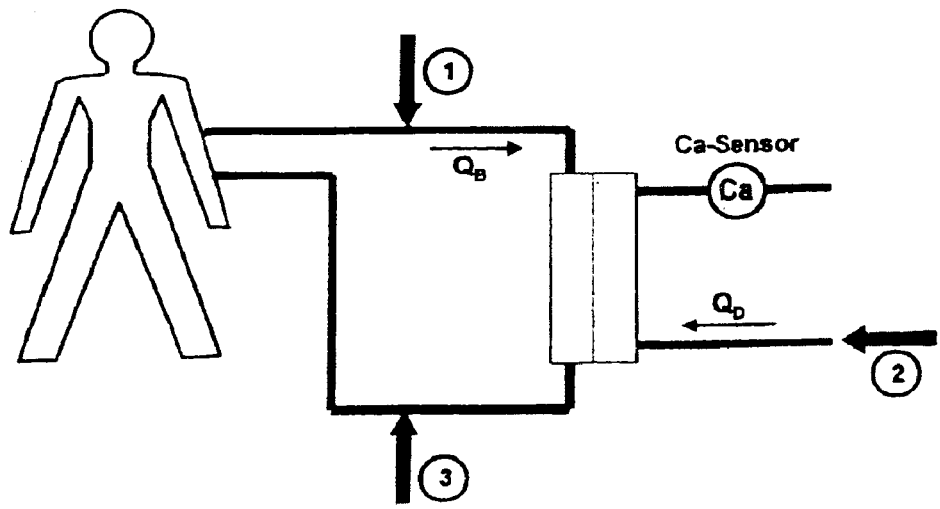
FIG. 2: a schematic illustration in accordance with FIG. 1 with an additional representation of a Ca ion sensor in the dialysate line leading away from the dialyser.

To carry out the method of the invention, the complexing of the Ca/citrate complex is prevented, for example, in that the addition of citrate is temporarily interrupted. The Ca concentration increases accordingly and the Ca ion concentration on the dialysate side can be measured by the Ca sensor visible in FIG. 2. The parameters $Q_D$ and $Q_B$ characterise the dialysate flow and blood flow respectively. A determination of the Ca ion concentration in the patient's blood is possible in that the dialysate flow is reduced by so much that the Ca ion concentration on the dialysate side is adapted to the Ca ion concentration on the blood side. The concentration on the blood side can be determined without a change to the blood flow and dialysate flow usual in the treatment from the measured concentration on the dialysate side also by means of the known above-mentioned relationships between the entry concentration of the Ca ions on the blood side, the measured starting concentration of the Ca ions on the dialysate side, the dialysate flow and the clearance.

Figure 3:
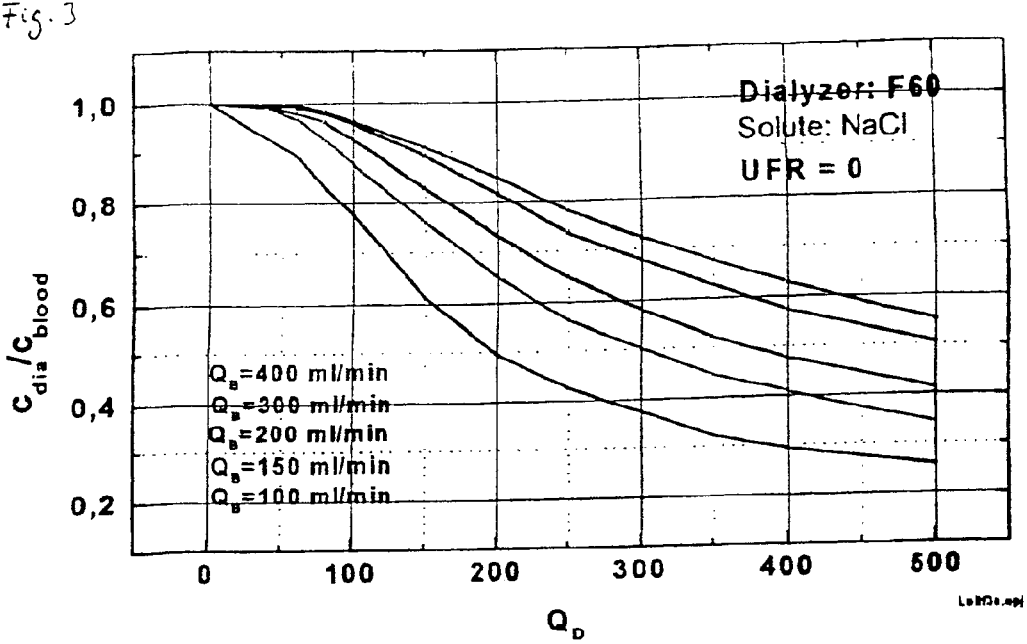
FIG. 3: a representation of the adaptation of the concentration on the dialysate side to the concentration on the blood side of an NaCl solution on reduction of the dialysate flow (in vitro experiment)

FIG. 3 shows the adaptation of the concentration of an NaCl solution on the dialysate side to the concentration on the blood side on a reduction of the dialysate flow. If the dialysate flow is selected to be sufficiently low—dependent on the blood flow, the relevant molecule and the dialyser used—the dialysate concentration practically corresponds to the blood concentration. The dialysate then reaches saturation. In this way, the concentration in the blood can be determined with good precision from the measured concentration in the dialysate.

Figure 4:
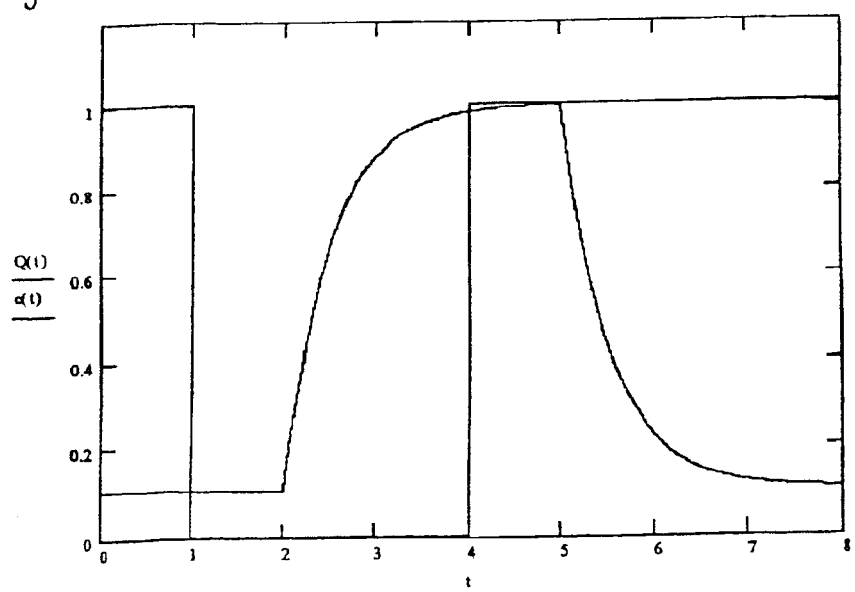
FIG. 4 a representation of the simulation of the concentration development to be expected in the dialysate with an intermittent interruption of the citrate infusion.

FIG. 4 shows the response function of the Ca ion concentration in the dialysate with an abrupt interruption of the citrate infusion. The rectangle function shown reproduces the time curve of the citrate infusion. As can be seen from FIG. 4, the citrate infusion is interrupted in the time interval t=1 to t=4. The other curve shown reproduces the concentration curve of Ca ions on the dialysate side. The ordinates of both figures and the abscissa have any desired units since it is not a question of absolute values here. After the infusion flow has been switched off (t=1), the low Ca ion concentration will initially still remain at the site of the sensor. The reason is that the volume of the hose connections acts as a dead volume between the infusion point and the position of the sensor. Dead times in the range from approximately 10 to 30 s are usual. As can further be seen from FIG. 4, the Ca ion concentration on the dialysate side subsequently increases. Due to the mixing of blood and dialysate with a respective high and low citrate concentration above all in the dialysate, the increase will not be sharp, but the concentration will approximate to an equilibrium value. The increase is illustrated in a simplified manner as an exponential function in FIG. 4. Usually, time constants from approximately 1 to 2 min can be anticipated with this. Then a quasi-stationary state is reached so that the concentration determined here can serve with good precision as the measured value. After the citrate infusion is turned back on (t=4), the dead time first becomes effective again. Subsequently, the Ca ion concentration falls in order to finally approximate to the low equilibrium value with an on-going citrate infusion.

FIG. 5 shows a method variant in which the interruption of the citrate infusion is not necessary. Here, the Ca ion concentration is determined in that the Ca ion is again released from the Ca citrate complex. This takes place by the supply of an acid (see Pos. 4). In this way, the pH is preferably reduced to a range from 2 to 3, which results in a dissociation of the complex and correspondingly releases the Ca ions. The advantage of this method variant is that no interruption of anti-coagulation takes place since the citrate addition is not interrupted.

The present invention makes it possible to monitor the actual physiologically relevant and critical parameters of the Ca ion concentration and the Mg ion concentration of the patient's blood during the whole therapy such that it is ensured at every point of the treatment that a state endangering the health of the patient is precluded. The prerequisite is naturally that the determination of the Ca ion value and of the Mg ion value takes place reliably. A good reliability can be achieved here by a redundant sensor embodiment or by sensors which perform self-tests. In addition to the use of sensors, other methods can naturally also be used to determine the ion concentration.

Whereas previously known monitoring systems generally only relate to individual technical components such as the monitoring of a pump with separate or integrated monitoring systems, for example droppers which allow the monitoring of an infusion, the monitoring of the ion concentration of the patient in accordance with the invention as the actual physiologically relevant critical parameter includes the whole therapy and thus takes every partial aspect of the method into account.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for determining ion concentration of blood of a patient in citrate anti-coagulated haemo-dialysis and/or haemo-filtration using a dialysate, comprising the steps of:

adding citrate to the blood circulation during citrate anti-coagulated haemo-dialysis and/or haemo-filtration;

temporarily interrupting the adding of citrate to the blood circulation to prevent complexing of a relevant ion with the citrate before measuring a concentration of said ion in the dialysate;

measuring the concentration of said ion in the dialysate; and determining the ion concentration of the blood on the basis of said measurement of the ion concentration in the dialysate.

2. The method in accordance with claim 1, wherein the measurement of the ion concentration in the dialysate is carried out after interrupting the citrate addition at the end of a length of time which is composed of a dead time caused by dead volumes and of a period of time required to reach a quasi-stationary state.

3. The method in accordance with claim 1, wherein the measurement of the ion concentration in the dialysate is carried out multiple times after interrupting the citrate addition and a measured value of said ion concentration is determined after reaching a quasi-stationary state.

4. The method in accordance with claim 1, wherein the measurement of the ion concentration is repeated multiple times after interrupting the citrate addition and a measured value of said ion concentration is determined by extrapolation of the ion concentrations obtained in the dialysate.

5. The method in accordance with claim 1, wherein the citrate concentration is interrupted for a pre-determined time interval and a measured value of said ion concentration is determined by integration of an area of a response function defined by the ion concentration in the dialysate as a function of time.

6. The method in accordance with claim 1, wherein the dialysate flow is reduced for the purpose of approximating the ion concentration of the dialysate to the ion concentration of the blood.

7. The method in accordance with claim 1, wherein the determination of the ion concentration of the blood takes place by calculation without reducing the dialysate flow.

8. The method in accordance with claim 1, wherein the detection of the ion concentration in the dialysate takes place by means of an ion-sensitive sensor in the dialysate flowing away from the dialyser.

9. The method in accordance with claim 1, wherein the determined ion concentration of the blood of a patient serves as a controlled variable whose value is influenced by control variables of citrate addition and/or addition of a substitution medium containing ions.

10. The method in accordance with claim 1, wherein an alarm is triggered when the determined ion concentration in the blood of the patient lies outside a permitted range or differs from a permitted value.

11. The method in accordance with claim 1, wherein the ion concentration in a compartment of the dialyser on the blood side thereof is determined without interrupting the citrate supply and is compared with a permitted threshold value of the ion concentration, with citrate feed being changed in dependence on this comparison.

12. The method in accordance with claim 1, wherein the ion includes calcium ions.

13. The method in accordance with claim 1, wherein the ion includes magnesium ions.

14. The method in accordance with claim 1, wherein the ion includes magnesium ions and calcium ions.

15. A method for determining ion concentration of blood of a patient in citrate anti-coagulated haemo-dialysis and/or haemo-filtration using a dialysate, comprising the steps of:

adding citrate to the blood circulation during a citrate anti-coagulated haemo-dialysis and/or haemo-filtration process, said citrate forming a complex with an ion;

lowering a pH of said dialysate to release said ion from said citrate complex before determining a concentration of said ion in the dialysate; and determining the ion concentration of the blood on the basis of the determination of the ion concentration in the dialysate.

16. The method in accordance with claim 15, wherein the pH is set to a range of pH=2–3.

17. The method in accordance with claim 15, wherein the setting of the pH in the dialysate takes place by means of an infusion of acid.

* * * * *